United States Patent [19]

Knapp, Jr.

[11] 4,045,470

[45] Aug. 30, 1977

[54] ALKYL ALLOPHANATES, METHOD FOR PREPARATION AND FUNGICIDAL USE OF THE SAME

[75] Inventor: Paul William Knapp, Jr., Bordentown, N.J.

[73] Assignee: American Cyanamid Company, Stamford, Conn.

[21] Appl. No.: 689,030

[22] Filed: May 24, 1976

[51] Int. Cl.² ........................................... C07C 149/40
[52] U.S. Cl. .............................. 260/470; 424/300; 424/309
[58] Field of Search ................................ 260/470

[56] References Cited

U.S. PATENT DOCUMENTS

| | | | |
|---|---|---|---|
| 3,763,219 | 10/1973 | Widdig et al. | 260/470 |
| 3,781,326 | 12/1973 | Mihalovski et al. | 260/470 |
| 3,790,619 | 2/1974 | Edamura et al. | 260/470 |
| 3,832,384 | 8/1974 | Mihailovski | 260/470 |
| 3,836,569 | 9/1974 | Wommack | 260/470 |

FOREIGN PATENT DOCUMENTS

| | | | |
|---|---|---|---|
| 1,214,415 | 12/1970 | United Kingdom | 260/470 |

*Primary Examiner*—Howard T. Mars
*Attorney, Agent, or Firm*—Harry H. Kline

[57] ABSTRACT

There are provided certain alkyl 3-thio-4{o-[(2,2,2-trihaloethylidene -or 2,2-dihaloalkylidene -or 2,2-dihalohaloalkylidene)amino]phenyl -or substituted phenyl}allophanates, a method for the preparation of the same, and the use of said allophanates as fungicidal agents.

1 Claim, No Drawings

ALKYL ALLOPHANATES, METHOD FOR PREPARATION AND FUNGICIDAL USE OF THE SAME

The present invention relates to certain novel alkyl 3-thio-4-{o-[(2,2,2-trihaloethylidene -or 2,2-dihaloalkylidene)amino]phenyl -or substituted phenyl}allophanates. More particularly, it relates to certain allophanates, to a method for the synthesis of said compounds, and to their use as fungicidal agents.

It is known that plant pathogenic fungi are directly responsible for, and cause significant, losses world-wide in agriculturally important food and fodder crops. In view of the fact that demands for food and fodder crops increase annually at a rapid rate, the control of fungi is, therefore, highly desirable.

As used herein, the term "food and fodder crops" is meant to include field crops such as grains, forage, pasturage, oil and seed crops, roots and tubers, sugar and horticultural crops such as tree fruits and citrus fruits, berries and grapes, nuts, vegetables, herbs and specialties such as ornamentals, flowers and the like.

According to the present invention, it has been found that certain allophanates, represented by formula (I), can be prepared:

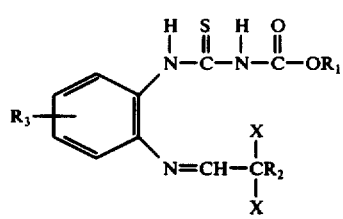

wherein $R_1$ is $C_1$–$C_5$ alkyl; $R_2$ is hydrogen, halogen, $C_1$–$C_3$ alkyl, or $C_1$–$C_3$ haloalkyl; $R_3$ is hydrogen, halogen, $C_1$–$C_4$ alkyl, or $C_1$–$C_4$ alkoxy; X is halogen, such as fluorine, chlorine or bromine. These are particularly effective for the control of plant pathogenic fungi and for protecting food and fodder crops from attack by said fungi.

As preferred compounds represented by formula (I), are those which include compounds wherein $R_1$ is $C_1$–$C_3$ alkyl; $R_2$ is hydrogen or halogen; $R_3$ is hydrogen, halogen, methyl, or methoxy; X is halogen. However, the most preferred compound is the methyl ester of 3-thio-4-{o[(2,2,2-trichloroethylidene)amino]phenyl}allophanic acid, represented by formula (Ia) below:

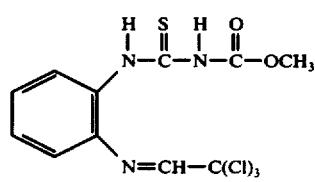

It possesses superior fungicidal efficacy.

In general, the compounds of formula (I) can be prepared in a straightforward manner by reacting one molar equivalent of the appropriate 4-(o-aminophenyl)-3-thioallophanic acid alkyl ester of formula (II) with a 1.5 to 10 molar excess of the appropriate aldehyde of formula (III) in the temperature range of 15° C to 100° C and, preferably, 25° C to 60° C for a period of time from 1 to 60 hours and, preferably, from 4 to 8 hours, in the absence or in the presence of a hydrocarbon solvent, such as hexane and heptane, benzene, toluene and xylene, or chlorinated hydrocarbons, such as methylene chloride, chloroform, dichloroethane and the like, or mixtures thereof. The above reaction can be graphically illustrated as follows:

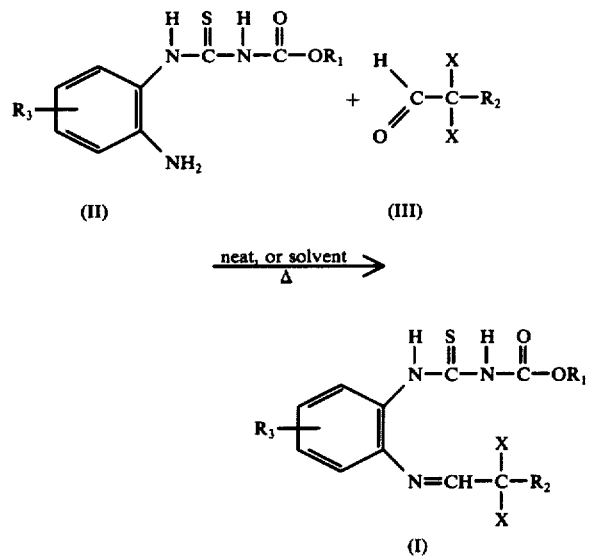

wherein $R_1$, $R_2$, $R_3$ and X are as hereinabove defined.

Alternatively, a compound of formula (I) can be readily prepared from a compound of formula (IV) by removing water therefrom, which involves heating said formula (IV) compound in a water immiscible aromatic solvent such as benzene, toluene and xylene in the presence of a catalytic amount of a dehydrating agent such as p-toluenesulfonic acid (p-TSA), zinc chloride and the like, and removing the water formed in the reaction by azeotroping the same from the reaction mixture. This reaction can be graphically illustrated as follows:

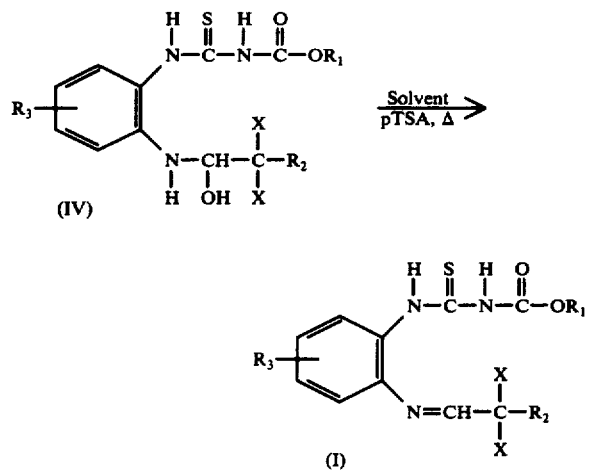

wherein $R_1$, $R_2$, $R_3$ and X are as defined above.

The preferred route for the preparation of formula (I) compounds, and especially for formula (Ia) compound, is however the hereinabove described condensation reaction of a formula (II) amine with a formula (III) aldehyde. The most preferred compound of the present invention represented by formula (Ia) is conveniently prepared by reacting one molar equivalent of 4-(o-aminophenyl)-3-thioallophanic acid methyl ester with a 1.5 to 10 molar excess of trichloroacetaldehyde, neat or in the presence of a solvent selected from the group of solvents listed above, at a temperature range of 15° C to 100° C and, preferably, between 25° C and 60° C for from 1 to 16 hours and, preferably, from 4 to 8 hours, as graphically illustrated below:

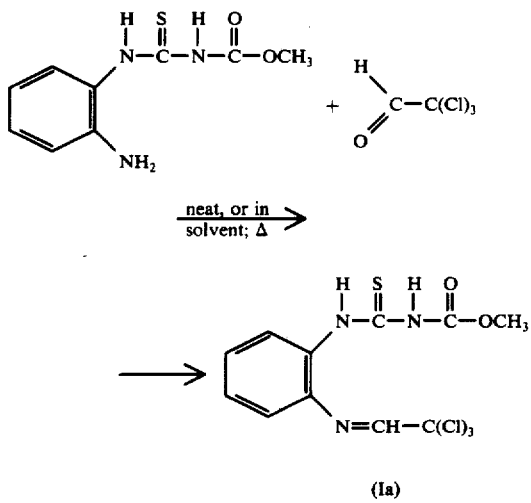

(Ia)

As stated above, the compounds of the present invention represented by formula (I) are particularly effective for the control of plant pathogenic fungi, and for protecting food and fodder crops from attack by said fungi. It is a good practice to formulate the compounds as dusts, dust concentrates, wettable powders, emulsion concentrates and the like.

Dusts can be prepared by grinding about 1% to 15% by weight of the active compound with about 99% to 85% by weight of an inert diluent such as attaclay, diatomaceous earth, kaolin, pumice, talc and the like.

Dust concentrates are made in similar fashion excepting that percent by weight of active ingredient is increased to from about 16% to 75% of the composition.

Wettable powders are prepared in the same manner as dust concentrates, but usually contain, in addition to the active ingredient and solid diluent, from about 1% to 5% by weight of a wetting agent such as sodium isopropylnaphthalene-sulfonate or the sodium salt of a sulfonated naphthalene formaldehyde condensate, and from about 1% to 5% by weight of a dispersing agent such as hydroxyethyl cellulose. A typical formulation would be 50% by weight of active ingredient, 2% of the dispersing agent, 5% of the wetting agent and 43% attapulgite.

Emulsion concentrates are prepared by dissolving 15% to 70%, by weight, of the compound in 85% to 30% of a solvent such as benzene, toluene, xylene, kerosene, 2-methoxy ethanol, propylene glycol, diethylene glycol, diethylene glycol monomethyl ether, formamide, methyl formamide and the like, and mixtures thereof. Advantageously, surfactants such as polyoxyethylated vegetable oil or an alkyl phenoxy polyoxyethylene ethanol are also incorporated in amounts of 1% to 5%, by weight, of said concentrate.

In using wettable powders or emulsion concentrates, the formulated material is generally dispersed in water and applied as a liquid spray to the above-said food and fodder crops, which are to be protected from attack by fungi. Usually the sprays applied to crops are used in sufficient quantity to provide about 0.15 to about 4.48 kg per hectare of active compound of formula (I).

The invention is further illustrated by the following examples which are not to be taken as being limitative thereof.

EXAMPLE 1

Preparation of Allophanic acid, 3-thio-4-{o-[(2,2,2-tri-chloroethylidene)amino]phenyl}-, methyl ester Chloral (100.2 g; 0.68 mole) is added to a suitable reaction vessel containing a solution of methyl 4-(o-aminophenyl)-3-thioallophanate (56.3 g; 0.25 mole) in hexane (312 ml). The reaction mixture is heated at 55° C to 60° C for 4 hours, cooled to 35° C and methylene chloride is added. The mixture is filtered and concentrated by evaporation until crystals appear. The slurry is then cooled to 5° C and filtered, and the isolated solid is washed with cooled methylene chloride to obtain 16.6 g of the methyl ester having a melting point equal to 160°–161° C.

Analysis Calculated for $C_{11}H_{10}Cl_3N_3O_2S$: C, 37.26; H, 2.84; Cl, 29.99; N, 11.85; S, 9.04. Found: C, 37.22; H, 2.85; Cl, 30.19; N, 11.77; S, 8.97.

Infrared, ultraviolet, mass, and $^1H$ and $^{13}C$ nuclear magnetic resonance spectra are consistent with the proposed structure. The product is homogeneous by thin layer chromatography.

EXAMPLE 2

Preparation of Allophanic acid-, 3-thio-4-{o-[(2,2,2-tri-chloroethylidene)amino]phenyl}-, methyl ester Methyl 4-(o-aminophenyl)-3-thioallophanate (294 g; 1.3 mole) is added over 1 hour to chloral (2.0 kg; 13.5 mole) and the mixture is stirred for an additional 2½ hours at room temperature. The reaction mixture is then poured into toluene (6.1 l) with stirring, and the resulting slurry is stirred for 30 minutes. The slurry is filtered and the isolated solid is washed with toluene (2×250 ml) and dried to afford 228 g of the title product (98% pure).

EXAMPLE 3

Preparation of Allophanic acid-, 3-thio-4-{o-[(2,2,2-tri-chloroethylidene)amino]phenyl}-, methyl ester Methyl 4-(o-aminophenyl)-3-thioallophanate (3.1 kg; 13.8 mole) is added over 90 minutes to chloral (12.7 kg; 86.2 mole) and the reaction mixture is stirred at room temperature for an additional 3 hours. The reaction mixture is then poured into toluene (44.5 l) and the slurry formed is stirred for 30 minutes. The slurry is filtered and the isolated solid is washed with toluene (2×2 l) and dried to afford 1.87 kg of the title product (95% pure).

EXAMPLE 4

Preparation of Substituted Alkyl Esters of Allophanic Acids

Repeating the procedure of Example 1, and using the appropriate formula (II) and formula (III) intermediates, a plurality of esters represented by formula (I) allophanate can be prepared. The intermediates and the products that are obtained are set forth in Table I below.

Table I

| Formula (II) Intermediate | Formula (III) Intermediate | Formula I Product |
|---|---|---|
| 2-aminophenyl-NH-C(=S)-NH-C(=O)-OCH$_3$ | OHC-CHCl$_2$ | 2-(N=CH-CHCl$_2$)phenyl-NH-C(=S)-NH-C(=O)-OCH$_3$ |
| 2-aminophenyl-NH-C(=S)-NH-C(=O)-OC$_2$H$_5$ | OHC-CCl$_3$ | 2-(N=CH-CCl$_3$)phenyl-NH-C(=S)-NH-C(=O)-OC$_2$H$_5$ |
| 4-Br-2-aminophenyl-NH-C(=S)-NH-C(=O)-OCH$_3$ | OHC-C(Cl)$_2$-CH$_3$ | 4-Br-2-(N=CH-C(Cl)$_2$-CH$_3$)phenyl-NH-C(=S)-NH-C(=O)-OCH$_3$ |
| 4-Cl-2-aminophenyl-NH-C(=S)-NH-C(=O)-OCH$_3$ | OHC-CH(Cl)$_2$ | 4-Cl-2-(N=CH-CH(Cl)$_2$)phenyl-NH-C(=S)-NH-C(=O)-OCH$_3$ |
| 4-C$_2$H$_5$O-2-aminophenyl-NH-C(=S)-NH-C(=O)-OC$_2$H$_5$ | OHC-C(Cl)$_2$-C$_2$H$_5$ | 4-C$_2$H$_5$O-2-(N=CH-C(Cl)$_2$-C$_2$H$_5$)phenyl-NH-C(=S)-NH-C(=O)-OC$_2$H$_5$ |
| 4-CH$_3$-2-aminophenyl-NH-C(=S)-NH-C(=O)-O(CH$_2$)$_2$CH$_3$ | OHC-C(Br)$_2$-CH$_3$ | 4-CH$_3$-2-(N=CH-C(Br)$_2$-CH$_3$)phenyl-NH-C(=S)-NH-C(=O)-O(CH$_2$)$_2$CH$_3$ |
| 4-(CH$_3$)$_2$CHO-2-aminophenyl-NH-C(=S)-NH-C(=O)-O(CH$_2$)$_4$CH$_3$ | OHC-C(Br)$_2$CHBrCH$_3$ | 4-(CH$_3$)$_2$CHO-2-(N=CH-C(Br)$_2$-CHBr-CH$_3$)phenyl-NH-C(=S)-NH-C(=O)-O(CH$_2$)$_4$·CH$_3$ |
| 4-F-2-aminophenyl-NH-C(=S)-NH-C(=O)-OCH$_3$ | OHC-C(Cl)$_3$ | 4-F-2-(N=CH-C(Cl)$_3$)phenyl-NH-C(=S)-NH-C(=O)-OCH$_3$ |
| 4-CH$_3$O-2-aminophenyl-NH-C(=S)-NH-C(=O)-OC$_2$H$_5$ | OHC-CCl$_3$ | 4-CH$_3$O-2-(N=CH-CCl$_3$)phenyl-NH-C(=S)-NH-C(=O)-OC$_2$H$_5$ |
| 3-CH$_3$O-2-aminophenyl-NH-C(=S)-NH-C(=O)-OCH$_3$ | OHC-CHCl$_2$ | 3-CH$_3$O-2-(N=CH-CHCl$_2$)phenyl-NH-C(=S)-NH-C(=O)-OCH$_3$ |
| 3-CH$_3$-2-aminophenyl-NH-C(=S)-NH-C(=O)-OCH$_3$ | OHC-CCl$_3$ | 3-CH$_3$-2-(N=CH-CCl$_3$)phenyl-NH-C(=S)-NH-C(=O)-OCH$_3$ |

Table I-continued

| Formula (II) Intermediate | Formula (III) Intermediate | Formula I Product |
|---|---|---|
| 2-bromo-aniline with N-C(=S)-N-C(=O)-OC$_2$H$_5$ and NH$_2$ group | O=C(H)-CBr$_3$ | 2-bromophenyl with N-C(=S)-N-C(=O)-OC$_2$H$_5$ and N=CH-CBr$_3$ |

EXAMPLE 5

To determine the effectiveness of allophanic acid, 3-thio-4-{o-[(2,2,2-trichloroethylidene)amino]phenyl}-, methyl ester as foliar fungicidal agent, a variety of pathogenic fungi, host plants and the said agent are employed in the following tests: Pathogens, host plants, the method of testing and the rating system used are reported below along with the data obtained:

Pathogens:
  *Piricularia oryzae* Carvara, the rice blast pathogen.
  *Venturia inaequalis* (Cke.) Wint., which causes apple scab.
  *Podosphaera leucotricha* (E&E) Salm. the cause of powdery mildew on apples and pears.
  *Erisiphe graminis f.* sp. hordei, the cause of powdery mildew on barley.
  *Phytophthora infestans* (Mont.) Dby, the late blight fungus of tomato and potato.

Host Plants:
  Rice (*Oryza sativa* cv. Nato)
  Barley (*Hordeum vulgare* cv. Larker)
  Apple (*Malus sylvestris*) (Seedling)
  Tomato (*Lycopersicon esculentum* cv. Bonny Best)

Plants are individually grown in 5 cm peat squares and assembled in 7.62 cm × 25.4 cm pressed fibre flats the week prior to spraying. With the exception of rice and barley, a single specimen of each species is used. A separate container is used for those plants in the mildew evaluation. The complete test system is shown below:

| Series 1 | Series 2 |
|---|---|
| Rice: Rice Blast | Apple: Powdery Mildew |
| Apple: Apple Scab | Barley: Powdery Mildew |
| Tomato: Late Blight | |

Spray solutions are prepared at final concentrations of 200, 100 and 50 ppm in 50 ml 50% aqueous acetone. In all cases acetone is added first to solubilize the compound and solutions made to final volume with deionized water.

Two containers, one from Series 1 and 2 (see above) are sprayed simultaneously on a turntable with 50 ml of the test solution. Spray is provided by 2 fixed Spray System Co. nozzles mounted to deliver vertical and horizontal solid cone patterns. Immediately thereafter, all plants are returned to the greenhouse to permit deposit to dry.

Plants in Series 1 and 2 are separately inoculated. Plants in Series 1 are inoculated with conidial suspension of the respective pathogens using a DeVilbiss paint sprayer operated at from 0.28 kg/cm² to 0.42 kg/cm² pressure and are transfered to a controlled temperature/humidity cabinet (ambient temperature; RH=95%). Plants in Series 2 are dusted with respective powdery mildew conidia and then removed to the greenhouse, to await disease development. All plants are rated for disease severity on a scale of 1-7 (clean-kill) as described below:

| Rating | Description |
|---|---|
| 1 | Nil |
| 2 | Trace disease |
| 3 | Slight disease |
| 4 | Moderate disease |
| 5 | Heavy disease |
| 6 | Severe disease |
| 7 | Kill |

In the accompanying tables, results are reported as percent disease control. Disease severity scores are converted to estimated (mean) percentages from tables, similar to those published by Eli Lilly and Co. (Elanco) for the 12 - point Barratt and Horsfall rating scores. Disease severity of treatments is converted to percent disease control according to the formula:

$$\frac{\text{Disease incidence control (\%)} - \text{Disease incidenct treatment (\%)}}{\text{Disease incidence Control (\%)}} \times 100 = \text{Percent Disease Control}$$

Table II

Series 1 - % Disease Control of Plants Sprayed to Run-off with Indicated Minimum Effective Rate (ppm)

| Compound | Rate | Rice Blast | Tomato Late Blight | Apple Scab |
|---|---|---|---|---|
| Allophanic acid-, 3-thio-4-{o-[(2,2,2-trichloroethylidene)amino]phenyl}-, methyl ester | 200 | 79 | 0 | 97 |
| | 100 | 30 | 0 | 95 |
| | 50 | 0 | 0 | 97 |

Table III

Series 2 - % Disease Control of Plants Sprayed to Run-off with Indicated Minimum Effective Rate (ppm)

| Compound | Rate | Apple Powdery | Barley Powdery |
|---|---|---|---|
| Allophanic acid-, 3-thio-4-{o-[(2,2,2-trichloroethylidene)amino]phenyl}-, methyl ester | 200 | 84 | 99 |
| | 100 | 84 | 99 |
| | 50 | 25 | 99 |

I claim:
1. The compound: allophanic acid-, 3-thio-4-{o-[(2,2,2-trichloroethylidene)amino]phenyl}-, methyl ester.

* * * * *